United States Patent
Palmunen et al.

(10) Patent No.: US 12,312,620 B2
(45) Date of Patent: May 27, 2025

(54) METHOD OF PRECIPITATING PHYTASE

(71) Applicant: AB Enzymes Oy, Rajamäki (FI)

(72) Inventors: Katja Palmunen, Rajamäki (FI); Mirkka Perkkalainen, Rajamäki (FI); Leena Lehtikari, Rajamäki (FI); Imke Kühn, Darmstadt (DE)

(73) Assignee: AB Enzymes Oy, Rajamäki (FI)

( * ) Notice: Subject to any disclaimer, the term of this patent is extended or adjusted under 35 U.S.C. 154(b) by 0 days.

(21) Appl. No.: 18/070,903

(22) Filed: Nov. 29, 2022

(65) Prior Publication Data
US 2023/0159909 A1     May 25, 2023

Related U.S. Application Data

(62) Division of application No. 17/288,676, filed as application No. PCT/FI2019/050788 on Nov. 6, 2019, now abandoned.

(30) Foreign Application Priority Data

Nov. 8, 2018   (EP) ..................................... 18205062

(51) Int. Cl.
C12N 9/96     (2006.01)
C12N 9/16     (2006.01)
(52) U.S. Cl.
CPC ............... *C12N 9/96* (2013.01); *C12N 9/16* (2013.01); *C12Y 301/03008* (2013.01); *C12Y 301/03026* (2013.01)

(58) Field of Classification Search
CPC ............... C12N 9/96; C12N 9/16; C12N 9/00
See application file for complete search history.

(56) References Cited

U.S. PATENT DOCUMENTS

2011/0189344 A1* 8/2011 Bodo ...................... C12N 9/98
                                                                  252/8.81
2021/0395719 A1   12/2021  Palmunen et al.

FOREIGN PATENT DOCUMENTS

| CN | 104125778 A | 10/2014 |
| CN | 107455477 A | 12/2017 |
| EP | 0969089 A1  | 1/2000  |
| WO | 2013119468 A2 | 8/2013 |

OTHER PUBLICATIONS

Griffiths et al. Protein extraction and 2-DE of water- and lipid-soluble proteins from bovine pericardium, a low-cellularity tissue. Nov. 2008, Electrophoresis.(22):4508-15. (Year: 2008).*
Tye et al., Molecular cloning and the biochemical characterization of two novel phytases from B. subtilis 168 and B. licheniformis, 2002, Appl Microbiol Biotechnol 59:190-197. (Year: 2002).*

(Continued)

*Primary Examiner* — Yong D Pak
*Assistant Examiner* — Naghmeh Nina Moazzami
(74) *Attorney, Agent, or Firm* — Elmore Patent Law Group, P.C.; Joseph C. Zucchero; Carolyn S. Elmore

(57) ABSTRACT

Herein is disclosed a process for effectively precipitating phytase as a complex with a polyanion, as well as compositions comprising phytase and a polyanion, and a method for manufacturing such compositions.

10 Claims, 5 Drawing Sheets

(56) References Cited

OTHER PUBLICATIONS

Demir et al., Phytase from Weissella halotolerans: purification, partialcharacterisation and the effect of some metals, 2017, International Journal of Food Properties, vol. 20, No. S2, S2127-S2137 (Year: 2017).*

Celem, E. B., "Purification of alpha-Galactosidase by Affinity Precipitation with Alginate", Prep Biochem. & Biotech., 38:4, 2008, 348-357.

Jain, S. et al., "Applications of Alginate in Bioseparation of Proteins", Artificial Cells, Blood Substitutes, and Biotechnology, 34:2, 2006, 127-144.

Mufwez, O. D. et al., "Preparation new immobilized phytase from *Bacillus* sp for improve its thermal stability", International Journal of ChemTech Research, vol. 10, No. 13, 2017, 333-338.

Pandey, A. et al., "Production, purification and properties of microbial phytases", Bioresource Technology, 77, 2001, 203-214.

Teotia, S. et al., "One-step purification of glucoamylase by affinity precipitation with alginate", J. Mol. Recognit., 14, 2001, 295-299.

\* cited by examiner

METHOD OF PRECIPITATING PHYTASE

RELATED APPLICATIONS

This application is a divisional of U.S. application Ser. No. 17/288,676, filed Apr. 26, 2021, which is a US National stage entry of International Application No. PCT/FI2019/050788, which designated the United States and was filed on Nov. 6, 2019, published in English and which claims priority to EP Application Serial No. 18205062.5, filed Nov. 8, 2018. The entire teachings of the above applications are incorporated herein by reference.

FIELD OF THE INVENTION

The present invention relates to the field of protein production, and in particular to concentrating phytase and to compositions comprising phytase.

BACKGROUND

Phytase enzymes (myo-inositol hexakisphosphate phosphohydrolases; EC 3.1.3.8 and 3.1.3.26) are a group of phosphatase enzymes that catalyze the hydrolysis of phytic acid (myo-inositol hexakisphosphate, also known as inositol polyphosphate, or phytate when in salt form) found in plants, especially in grains and oil seeds. The majority (50-70%) of dietary phosphate is bound to phytic acid with low availability for non-ruminant animals.

Phytases are able to degrade phytate (myo-inositol hexakisphosphate), which results into release of inorganic phosphorus. Simultaneously, compounds bound to the phytate are also released. Thus, phytases can be used to increase nutritional value of feed by releasing inorganic phosphate and other nutrients from phytate. In animal feeding supplementing feed with phytase also helps to decrease environmental impact of farming, because phytate bound phosphorus can be utilized by the animal, which reduces the amount of mineral phosphorus to be added and the phosphorus excretions to the manure.

Most commercially available phytases are histidine acid phosphatases (HAPs). They are further divided into 6-phytases (mostly bacterial phytases that initiate the dephosphorylation of phytic acid at position 6') and 3-phytases (mostly fungal phytases that initiate the dephosphorylation of phytic acid at position 3') based on the phosphorus position they primarily hydrolase first (usually referring to the D-configuration of the molecule).

Protein precipitation is commonly used in downstream processing of biological products in order to concentrate and purify proteins from various impurities. Protein precipitation is a process where a protein is separated from a solution as a solid by altering the protein solubility with addition of a specific reagent. Repulsive electrostatic forces between proteins are manipulated by the reagent to favor generation of submicroscopic sized protein aggregates. The aggregates grow and stick to each other forming eventually microscopic amorphous precipitate particles lacking well-ordered structure or in a special case crystalline particles having well-ordered structure. If solids concentration is high enough these particles can be seen with bare eye as for example haziness, turbidity, flocs or sediment in the liquid.

SUMMARY

The inventors have surprisingly found that phytase can be precipitated by a simple method, which is applicable in large scale production of phytase. The method can be used e.g. to precipitate and concentrate phytase from spent fermentation broth, and to separate phytase from other components present in the spent fermentation broth. Further, the method can be applied to manufacture concentrated phytase compositions. The phytase-polyanion complex formed by the present method is stable which makes it possible e.g. to wash the phytase-polyanion complex. After precipitation, it is also possible to formulate the phytase-polyanion complex into various formulations. The precipitate can also be reconstituted to a liquid product in selected conditions.

According to a first aspect of the invention is provided a method of precipitating phytase comprising
  i. providing an aqueous medium comprising phytase; and
  ii. adding a polyanion.

The present method is very fast, inexpensive and effective, and it solves problems relating to previous methods that involve ultrafiltration or other purification steps to increase phytase concentration. Thus, the present invention simplifies production of phytase compositions.

Without being bound to any particular theory, the invention is based on the discovery that phytase is capable of forming a complex with polyanions, resulting into controlled and effective precipitation of phytase. The complex formation can be controlled by selecting conditions, such as concentration, the type of polyanion, ionic strength, and pH. This present invention can be utilized in production of phytase-containing products e.g. by precipitating phytase from spent fermentation broth while leaving other components in a soluble form. The precipitated phytase-polyanion complex is stable, allowing e.g. concentrating and washing to further increase purity without marked decrease in yield. Advantageously, the phytase-polyanion complex precipitated with the present method can also be dissolved after precipitation with excellent yield. Further, the precipitate provides phytase in a very stable form and even allows dehydrating and reconstituting without significant changes in specific activity or yield.

According to the second aspect of the invention is provided a method of preparing a phytase composition comprising
  i. providing an aqueous medium comprising phytase;
  ii. adding a polyanion for precipitating phytase as a complex of phytase and polyanion; and
  iii. recovering the precipitated phytase to obtain the phytase composition.

According to another aspect of the invention is provided a method of preparing a phytase composition comprising:
  i. providing an aqueous medium comprising phytase;
  ii. adding a polyanion for precipitating phytase; and
  iii. recovering the precipitated phytase to obtain the phytase composition.

According to the third aspect of the invention is provided a phytase composition comprising phytase complexed with a polyanion.

According to the fourth aspect is provided a phytase composition comprising phytase and a polyanion.

According to an aspect is provided a feed supplement comprising phytase composition of the third or fourth aspect and optionally at least one further enzyme.

FIGURES

Figure 7:
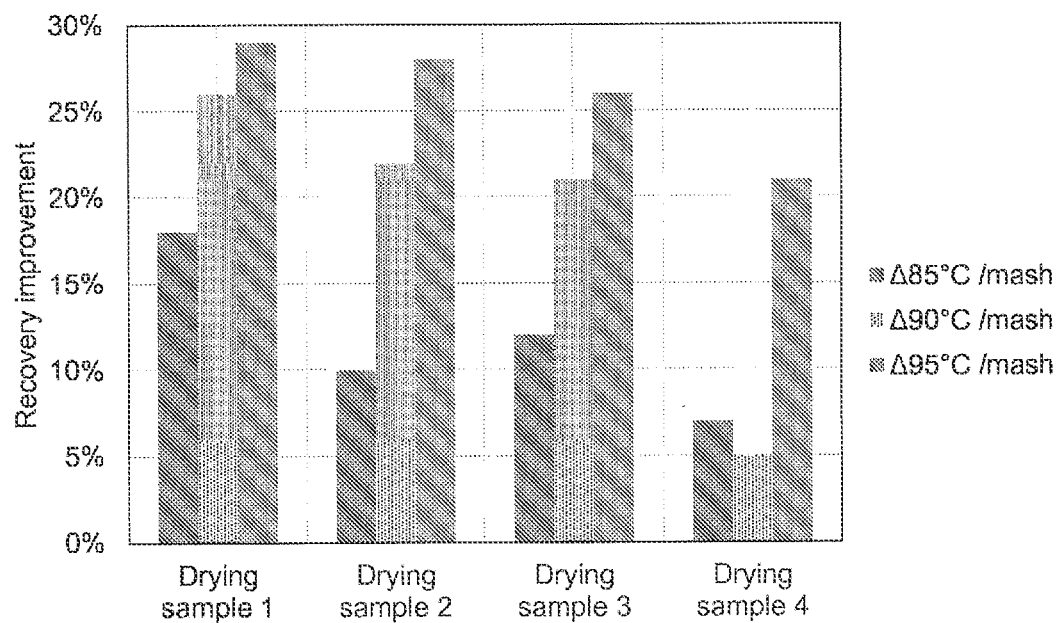

FIG. 7 is a diagram showing recovery improvement in pelleting test when polyelectrolyte precipitated and spray dried phytase powder formulations are compared to the commercial dry phytase products without polyelectrolyte precipitation. For recovery the enzyme activity analysed in feed pellets after heat treatment by conditioning at different temperatures before pelleting is compared to the enzyme activity in the mash feed without heat treatment and pelleting.

Figure 8:
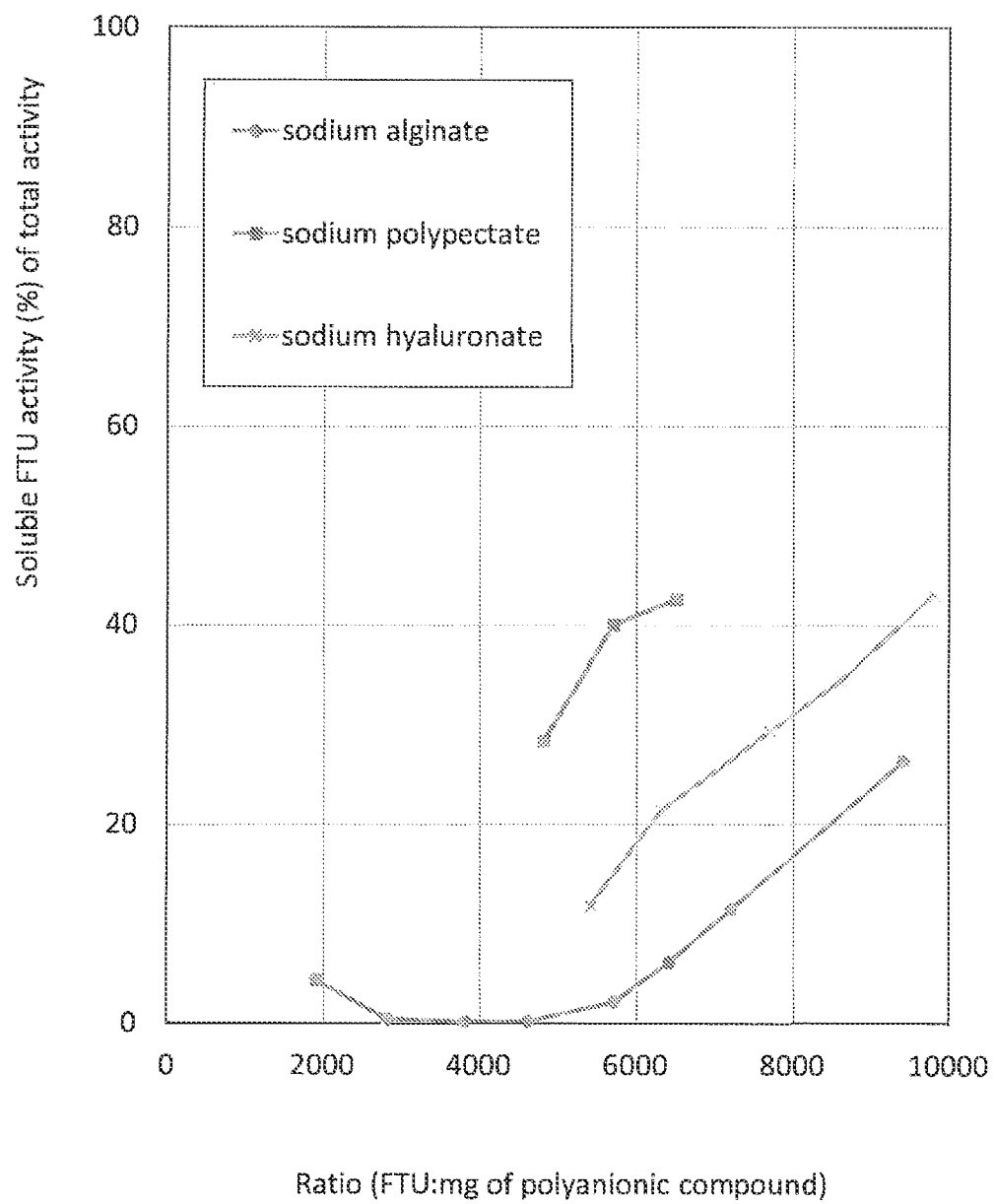

FIG. 8 is a diagram showing the effect of phytase:mg of polyanionic compound-ratio and different polyanionic compounds on soluble phytase activity.

DETAILED DESCRIPTION

In an embodiment the aqueous medium comprising phytase comprises fermentation broth, preferably clarified spent fermentation broth.

In another embodiment the aqueous medium comprising phytase is fermentation broth, preferably clarified spent fermentation broth.

In an embodiment the clarified spent fermentation broth is obtained by clarifying spent fermentation broth from recombinant production of the phytase.

In an embodiment the aqueous medium comprising phytase comprises clarified fermentation broth, spent fermentation broth, spent and clarified fermentation broth, or a combination thereof.

In an embodiment the dry matter content of the aqueous medium comprising phytase without solids is between 0.1-25% w/w before adding the polyanion.

In another embodiment the dry matter content of the aqueous medium comprising phytase without solids is selected from the range 0.1-25% w/w, such as 0.1-20, 0.1-15, 0.1-10, 1-20, 1-15, 1-10, 2-20, 2-15, 2-10, 3-20, 3-15, 3-10, 3-9, 3-8, 4-15, 4-10, 4-9 or 4-8% w/w. In an embodiment the dry matter content refers to the dry matter present in the aqueous solution comprising phytase without calculating the effect of the added polyanion.

In an embodiment the aqueous medium comprising phytase does not contain $CaCl_2$, or the concentration of $CaCl_2$) is below 5 mM, 2 mM or 1 mM.

In an embodiment the pH is set to 3-5 for enhancing precipitation of phytase.

In an embodiment the pH is set to a value selected from the range 3-5. The pH can be set to the selected pH before adding the polyanion. In another embodiment the pH is set to the selected value after adding the polyanion. Preferably the pH is maintained near the selected value until the end of precipitation.

In an embodiment the pH is set and optionally maintained at range 3-5, such as 3-4.9, 3-4.8, 3-4.7, 3-4.6, 3-4.5, 3-4.4, 3-4.3, 3-4.2, 3-4.1, 3-4, 3-3.9, 3-3.8, 3.1-4.9, 3.1-4.8, 3.1-4.7, 3.1-4.6, 3.1-4.5, 3.1-4.4, 3.1-4.3, 3.1-4.2, 3.1-4.1, 3.1-4, 3.1-3.9, 3.1-3.8, 3.2-4.9, 3.2-4.8, 3.2-4.7, 3.2-4.6, 3.2-4.5, 3.2-4.4, 3.2-4.3, 3.2-4.2, 3.2-4.1, 3.2-4, 3.2-3.9, 3.2-3.8, 3.3-4.9, 3.3-4.8, 3.3-4.7, 3.3-4.6, 3.3-4.5, 3.3-4.4, 3.3-4.3, 3.3-4.2, 3.3-4.1, 3.3-4, 3.3-3.9, or 3.3-3.8, or at about 3, 3.1, 3.2, 3.3, 3.4, 3.5, 3.6, 3.7, 3.8, 3.8, 3.9, 4, 4.1, 4.2, 4.3, 4.4, 4.5, 4.6, 4.7, 4.8, 4.9, or 5.

In an embodiment the polyanion is a polyanion salt, preferably a Na salt of the polyanion. Alternatively, the polyanion is a salt with another monovalent, such as a K salt.

In an embodiment the polyanion is alginic acid, pectic acid, hyaluronic acid, phytic acid, or a salt of such a polyanionic acid, or any combination thereof.

In an embodiment the polyanion is a polyanionic salt. In an embodiment the polyanion is Na alginate, Na polypectate, Na hyaluronate, Na phytate or a combination thereof, or a combination of the polyanionic salt with at least one polyanion.

In an embodiment the salt of the polyanionic acid is added in a solid form or as an aqueous solution to the aqueous solution comprising phytase.

In an embodiment the polyanion salt is added in a solid form to the aqueous solution comprising phytase.

In an embodiment the method comprises controlling pH by keeping it in the range 3-5, preferably in the range 3.1-4, after adding the polyanion. In an embodiment the precipitated phytase is washed.

In an embodiment the precipitated, optionally washed, phytase is dehydrated to obtain a dry product.

In an embodiment the dry product is in the form of a pellet, extrudate, granule, powder or a coated product.

In an embodiment dehydration is done by protein drying technique known in prior art including but not limited to spray drying, freeze drying, vacuum drying, evaporating, spray coating, granulation or extrusion. Optionally the precipitated phytase is supplemented with a drying additive before drying. Suitable drying additives include but are not limited to sugars like trehalose, sugar alcohols, salts and polymers like polyethylene glycol, such as PEG 4000. However, the precipitate formed by the present method is suitable for drying also without a drying additive, because of the good stability of the precipitated complex.

In an embodiment the precipitated, optionally washed, phytase is suitable to be used in compositions that are cross-linked, immobilized or encapsulated using techniques known in prior art.

In an embodiment the precipitated, optionally washed, phytase is suitable to be used as such or at least partially dissolved form in dilute or compressed solid or liquid compositions including but not limited to solutions, suspensions, emulsions, semi-solids, solids, pastes, pellets, cakes, gels, tablets, films or coatings having certain targeted properties like for example controlled rheology, viscosity or enzyme release using techniques known in prior art.

In an embodiment the method comprises dissolving the precipitated phytase to obtain a liquid product. Such a liquid product thus comprises phytase and the selected polyanion used in the precipitation.

In an embodiment the method comprises dissolving the dry product. This is advantageous to obtain a reconstituted product having a high concentration.

In an embodiment the ratio of phytase to polyanion expressed as FTU:mg polyanion is selected from the range 500-15000.

In an embodiment the ratio expressed as FTU:mg polyanion is selected from the range 500-15000, 1000-14000, 1500-13000, or 2000-12000.

In an embodiment the amount of the added polyanion is 0.001-2% w/w based on dry matter content.

In an embodiment the polyanion is added in an amount of 0.001-2, 0.005-2, 0.01-2, 0.1-2, 0.001-1.5, 0.005-1.5, 0.01-1.5, 0.1-1.5, 0.001-1, 0.005-1, 0.01-1, or 0.1-1% w/w based on dry matter content.

In an embodiment the polyanion is an alginic acid, a pectic acid, a hyaluronic acid, a phytic acid or a salt of such an acid, preferably a salt with a monovalent cation.

In another embodiment the polyanion is a combination of phytic acid or its salt together with a polyanion selected from alginic acid, pectic acid, hyaluronic acid, or a salt of such an acid. It is preferable to use a further polyanion when phytic acid, or its salt, is used to keep the phytase-polyanion complex stable for a longer time. This is particularly useful when precipitating phytase with phytic acid or its salt in conditions where the phytase has enzyme activity.

In an embodiment the salt is an alginate salt, a polypectate salt, a hyaluronate salt, a phytate salt or any combination thereof. In an embodiment said salt is a Na salt, K salt, $NH_4$ salt or Ca salt, preferably a Na salt.

In an embodiment the composition is a liquid product or a dry product.

In an embodiment the precipitated phytase is harvested by sedimentation, decantation, centrifugation, filtration, or a combination thereof. The precipitated phytase is preferably harvested in a small volume. This allows recovering the precipitated phytase in a high concentration and specific activity.

Advantageously precipitating and/or concentrating phytase by the present method offers a simple way to improve cost efficiency in the production of concentrated phytase products compared to the current concentrating methods by ultrafiltration that does not remove high molecular weight impurities. The precipitate can optionally be washed and then dissolved by increasing ionic strength of the medium above 0.25 M and adjusting pH above 4. This is particularly useful to manufacture compositions in which the final formulation is liquid. Such liquid of dissolved precipitate or precipitate suspension without dissolving step are both equally useful to de dried e.g. with spray drying if dry product is the desired final formulation.

In an embodiment the ionic strength of the aqueous medium comprising phytase is below 0.25 M before adding polyanion.

In an embodiment ionic strength is kept below 0.25 M after adding polyanion to keep phytase in non-soluble form.

In an embodiment dissolving the precipitated phytase is carried out in the presence of $CaCl_2$. Adding of $CaCl_2$ to precipitated phytase is advantageous because it dissolves the phytase-alginate complex in below 0.25M concentrations, as shown in Example 24. In an embodiment $CaCl_2$ is added to dissolve the precipitated phytase preferably in an amount of 70 mM, 40 mM or less, and more preferably in an amount of at least 10 mM, 20 mM or 30 mM. $CaCl_2$ is an advantageous agent compared other salts such as sodium chloride or sodium sulphate, because the other salts are needed in much higher concentrations such as 250 mM to solubilise the precipitated phytase.

In an embodiment the phytase is a recombinant phytase.

In an embodiment the phytase is *E. coli* phytase, *Aspergillus* phytase or *Buttiauxella* phytase., preferably a phytase having phytate degrading activity.

In an embodiment at least one component of the phytase composition, preferably the phytase enzyme, has a different structural or physical characteristic compared to a corresponding natural component from which at least one component is derived from. In an embodiment the characteristic is uniform size, homogeneous dispersion in the composition, non-native glycosylation, non-native stability, production level, or purity. In an embodiment the phytase composition comprises a phytase-polyanion complex. Such a complex does not occur in a natural environment of phytases. In the present invention such a complex is however possible to achieve. Factors contributing to the complex formation are concentration of phytase and polyanion, pH, and ionic strength and temperature.

In an embodiment the phytase is a bacterial phytase, preferably a bacterial recombinant phytase expressed in a heterologous host cell.

In an embodiment the phytase is a 6-phytase having enzyme activity for 6-phos, preferably a protein engineered variant, chimeric or hybrid phytase. In another embodiment the hybrid phytase comprises phytases that are engineered to contain elements of two or more phytases. In an embodiment the phytase is a fungal phytase, preferably a fungal recombinant phytase expressed in a heterologous host cell.

In an embodiment the phytase is a 3-phytase, preferably a protein engineered variant, chimeric or hybrid phytase. In another embodiment the hybrid phytase comprises phytases that are engineered to contain elements of two or more phytases.

In an embodiment the polyanion is selected such that it is capable of forming a reversible phytase-polyanion complex. Preferable examples of suitable polyanions are alginic acid, a pectic acid, a hyaluronic acid, and phytic acid or a salt of the acid or any combination thereof. These and other polyanions can also be found in for example naturally occuring polysaccharides, gums or hydrogels like xanthan gum, gum arabic, heparin or carrageenan, or synthetic compounds having corresponding functions or characteristics.

In an embodiment pH of the aqueous solution of phytase is set to 3-5 before adding the polyanion.

In an embodiment pH is controlled after adding polyanion by setting and/or keeping it at 3-5.

In an embodiment the polyanion is added as a buffered aqueous solution. In an embodiment the solution is buffered to pH selected from the range 3-5.

In an embodiment the precipitated phytase is recovered by microfiltration, belt filtration, centrifugation, dynamic cross flow filtration, sedimentation, or any combination thereof. Preferably the precipitated phytase is recovered by microfiltration or centrifugation.

Because the phytase-polyanion complex obtained with the present method is stable, it is possible to wash the precipitated phytase. Thus, it is possible to use the method to remove other components present e.g. in a spent fermentation broth to which phytase is produced in recombinant production. For example macromolecules such as proteins other than phytase, carbohydrates and cellular debris can be removed by washing. Also small molecule components present in the spent fermentation broth can be removed by washing. Washing is advantageous also to effectively remove microbiological material from the phytase composition.

In an embodiment the aqueous solution comprising phytase contains recycled supernatant obtained by concentrating phytase and recovering the supernatant to be used as the recycled supernatant.

In an embodiment washing is carried out by using a buffer solution having pH and/or ionic strength close to the pH and/or ionic strength used in the precipitation step.

In an embodiment ionic strength of the wash solution is lower than used in the precipitation of the phytase.

In an embodiment pH of the wash solution having ionic strength below 0.25 M is lower or higher than used in the precipitation step. Preferably the pH is higher or lower by at least 1 pH unit, such as 1.5 or 2 pH units.

In an embodiment pH is controlled by setting it to a value selected from a suitable range for precipitation of a certain phytase. This can be determined by the skilled person by carrying out the present method at various pH values and calculating precipitation yield and/or specific activity at each pH. Example 2 provides an example of calculating precipitation yield. Suitable range can then be selected based e.g. on the desired yield and/or specific activity obtained at a given pH.

In an embodiment phytase enzyme activity is determined using the method disclosed in Example 1.

In an embodiment the method is an industrial scale method.

In an embodiment the method is carried out in the sequence specified in a claim, aspect or embodiment.

In an embodiment FTU is determined according to ISO 30024:2009(E).

EXAMPLES

Example 1—Phytase Enzyme Materials and Analytic Methods

Enzyme materials used for polyelectrolyte precipitations were different phytase sources, an *E. coli* phytase, an *Aspergillus* phytase and a *Buttiauxella* phytase. All these phytases were expressed in *Trichoderma reesei* fungus. Precipitations of *E. coli* phytase or *Aspergillus* phytase were started using either clarified spent fermentation broths or concentrates of them, containing preservative to prevent microbial contaminations, from several different fermentations of phytase protein. Spent fermentation broths were clarified by filtration and concentrated with 10 kDa ultrafiltration membrane to increase protein concentration. Precipitation of *Buttiauxella* phytase was done using purified enzyme liquid from dried granule as starting material. Enzyme activity of the protein was measured as the release of inorganic phosphate from sodium phytate (0.98% (w/v) phytate at 37° C. in 250 mM sodium acetate buffer at pH 5.50 in 60 min (FTU activity; ISO 30024:2009(E) Animal feeding stuffs—Determination of phytase activity). Protein concentration was measured with Bio-Rad Protein Assay that is based on the colour change of Coomassie brilliant blue G-250 dye in response to various protein concentrations. The Coomassie blue dye binds to primarily basic and aromatic acid residues, especially arginine. Used reagents for the assay were Bio-Rad Protein Assays Dye Reagent Concentrate (Bio-Rad No. 500-0006) and bovine gamma globulin protein standard (Bio-Rad Protein Assay Standard I. No. 500-0005).

Example 2—Reversible Phytase-Alginate Complex Formation by Polyelectrolyte Precipitation in Batch Process Four batch precipitations were done using concentrates of *E. coli* phytase as enzyme material. Three of these were repeated batch precipitations where buffered polyanion containing reagent solutions were prepared by adding 1 M sodium acetate buffer (nominal pH 3.6) and dry sodium alginate in tap water. In one of the batch precipitations sodium citrate was used as buffer instead of sodium acetate. Dry alginate powder was let to dissolve and the reagent solutions were stored in cold room overnight. Next day phytase enzyme concentrate was added to the reagent solutions at room temperature while stirring properly with magnetic stirrer, whereupon phytase-alginate complex was rapidly formed. This was observed as heavy, slightly fibre like and almost white precipitate that formed during phytase adding. Precipitations were let to continue for an hour in cold room. After this samples were taken to analyse enzyme activities. Final precipitation conditions and activity yields are represented in table 1. Needed tap water and concentrate amounts were calculated so that aimed FTU:mg of sodium alginate-ratio and calculated dry matter contents were reached. Precipitation yields were calculated based on soluble phytase activity analysed in supernatants after precipitate separation by centrifugation compared to the total activity. These results show that phytase can be precipitated from concentrate of clarified spent fermentation broth with high yield using alginate as polyanionic precipitant.

TABLE 1

Precipitation conditions and yields of four *E. coli* phytase precipitation batches.

| Precipitation batch | Volume (ml) | Sodium acetate (M) | Sodium alginate (% w/w) | Aimed FTU:mg of sodium alginate - ratio | Calculated dry matter (% w/w) | Precipitation yield (%) |
|---|---|---|---|---|---|---|
| 1 | 1 500 | 0.05 | 0.17 | 10 000 | 5.1 | 76 |
| 2 | 1 500 | 0.05 | 0.17 | 10 000 | 5.1 | 75 |
| 3 | 2 000 | 0.05 | 0.18 | 10 000 | 5.0 | 81 |
| 4 | 1 000 | * | 0.20 | 10 000 | 6.0 | 77 |

*Instead of 0.05M sodium acetate buffer batch contained 1% (w/w) tri-sodium citrate dihydrate and 0.7% citric acid, anhydrous.

Example 3—Effect of Ionic Strength on Yield of Precipitated Phytase

Figure 1:
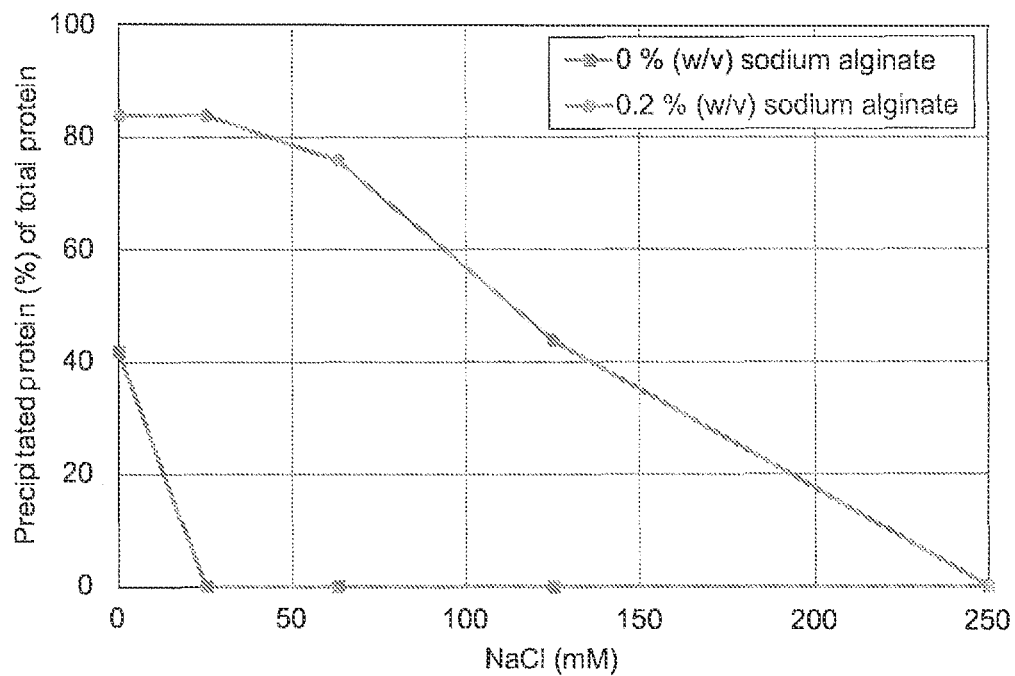
FIG. 1 is a diagram showing the effect of sodium chloride and sodium alginate on the precipitation of *E. coli* phytase protein.

Experiments were done using concentrate of *E. coli* phytase as enzyme material. To study the effect of ionic strength and sodium alginate on precipitation yield a series of precipitation experiments were performed at room temperature. Experiments were made in 15 ml tubes and total volumes of the experiments were 10 ml. Reagent solutions were prepared by mixing 5 M sodium chloride, 0.4% (w/w) sodium alginate and tap water in tubes. Half of the experiments were performed with sodium alginate and half without sodium alginate. 2 ml of phytase concentrate was added to the tubes and mixed immediately to enable complex formation. Experiments were done without pH adjusting. Measured pH varied from 4.3 to 4.7. The resulting soluble and total protein concentrations were determined. Final precipitation conditions and yields are represented in table 2 and illustrated graphically in FIG. 1. Precipitation yields were calculated based on soluble protein concentration in supernatants compared to the total protein concentration. These results show clearly strong precipitation effect of low ionic strength and added sodium alginate.

TABLE 2

Effect of ionic strength and sodium alginate on the precipitation of *E. coli* phytase protein.

| Experiment | NaCl (mM) | Na-alginate (% w/v) | Observations | Precipitation yield (%) |
|---|---|---|---|---|
| 1 | 250 | 0 | clear solution | 0 |
| 2 | 125 | 0 | clear solution | 0 |
| 3 | 63 | 0 | clear solution | 0 |
| 4 | 25 | 0 | clear solution | 0 |
| 5 | 0 | 0 | precipitated suspension | 42 |
| 6 | 250 | 0.2 | clear solution | 0 |
| 7 | 125 | 0.2 | precipitated suspension | 44 |
| 8 | 63 | 0.2 | heavy precipitate | 76 |
| 9 | 25 | 0.2 | heavy precipitate | 84 |
| 10 | 0 | 0.2 | heavy precipitate | 84 |

Example 4—Precipitation Directly from Clarified Spent Fermentation Broth

Batch precipitations were done using clarified spent fermentation broth of *E. coli* phytase as enzyme material. Using the method in example 2 two repeated 2000 ml scale batch precipitations were done to study precipitation directly from clarified spent fermentation broth containing only added preservative to see an effect of phytase concentration and starting material quality on precipitated phytase yield. In these precipitations also different sodium alginate type and FTU:mg of sodium alginate-ratio were used. Final precipitation conditions and activity yields are represented in table 3. Needed tap water and concentrate amounts were calculated so that aimed FTU:mg of sodium alginate-ratio and calculated dry matter contents were reached. Precipitation yields were calculated based on soluble enzyme activities in supernatants compared to the total phytase activity. These results show that polyelectrolyte precipitation directly from clarified spent fermentation broth is possible with high yield.

TABLE 3

Precipitation conditions and yields of two *E. coli* phytase - polyelectrolyte precipitation batches.

| Precipitation batch | Sodium acetate (M) | Aimed FTU:mg of sodium alginate -ratio | Calculated dry matter (% w/w) | Precipitation yield (%) |
|---|---|---|---|---|
| 5 | 0.05 | 4 000 | 2.1 | 96 |
| 6 | 0.05 | 4 000 | 2.1 | 88 |

Example 5—Precipitation During Concentration

Phytase precipitation was done using clarified spent fermentation broth of *E. coli* phytase as enzyme material. Using the same FTU:mg of sodium alginate ratio as in the example 2 the precipitation was performed simultaneous with ultrafiltration step that is normally used to concentrate proteins of clarified spent fermentation broths. This was continued with buffer exchange and two washing steps. Different steps are represented in table 4. First dry sodium alginate was added slowly to clarified spent fermentation broth while stirring properly with magnetic stirrer. Precipitate formation started during sodium alginate addition and it was let to proceed in the next steps. The clarified spent fermentation broth containing phytase-alginate precipitate was concentrated by ultrafiltration. When 1.5 times concentration was reached, the diafiltration step was started by adding 40 mM sodium acetate buffer (nominal pH 3.6) slowly to the retentate while stirring properly with magnetic stirrer. Diafiltration was continued until 1.3 times concentration was reached. In the next step double washing was made using tap water. In the last step double washing was made by microfiltration. The aim of this step was to wash out other proteins and high molecular weight compounds and keep phytase inside the membrane as a solid complex. Calculated phytase yield of this combined precipitation, concentration and harvesting test was 72% analysed based on activity in the retentate after microfiltration. Specific phytase activity was 40% higher in the final retentate than in the clarified spent fermentation broth. These results show that alginate precipitation can be made simultaneous with ultrafiltration.

TABLE 4

Description of filtration steps during concentration and washing of precipitated *E. coli* phytase.

| Step | | Membrane MWCO | Added solution | Concentration factor |
|---|---|---|---|---|
| 1 | Ultrafiltration | 10 kDa | | 1.5x |
| 2 | Diafiltration | 10 kDa | 40 mM sodium acetate | 1.3x |
| 3 | Washing | 10 kDa | tap water | 1.1x |
| 4 | Washing and microfiltration | 0.2 μm | tap water | 1.9x |

Example 6—Precipitate Harvesting by Microfiltration

Figure 2:
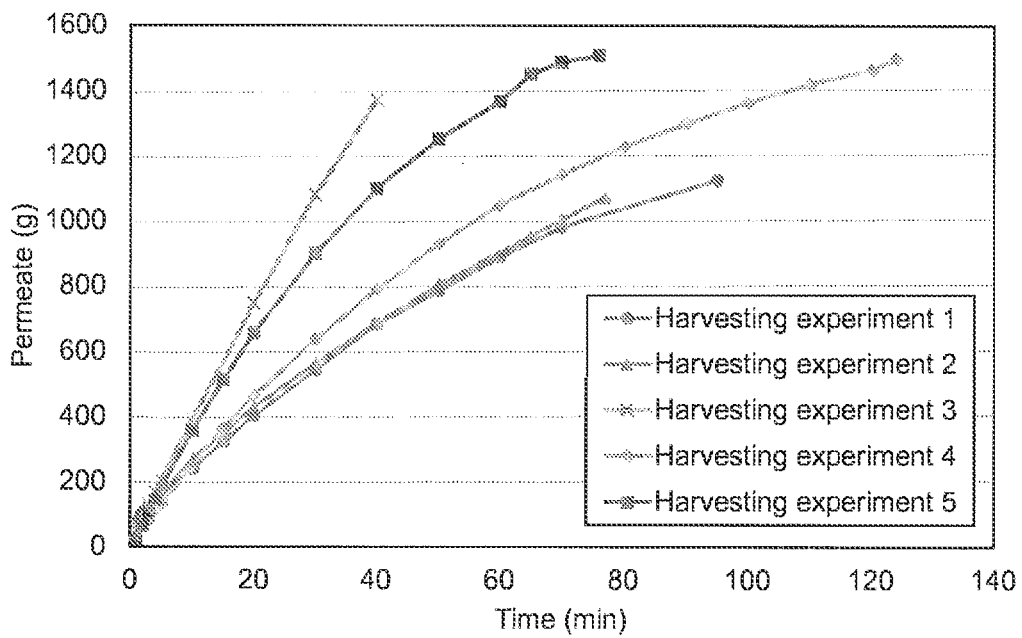
FIG. 2 is a diagram showing permeate formation during precipitated phytase harvesting by microfiltration.
Figure 3:
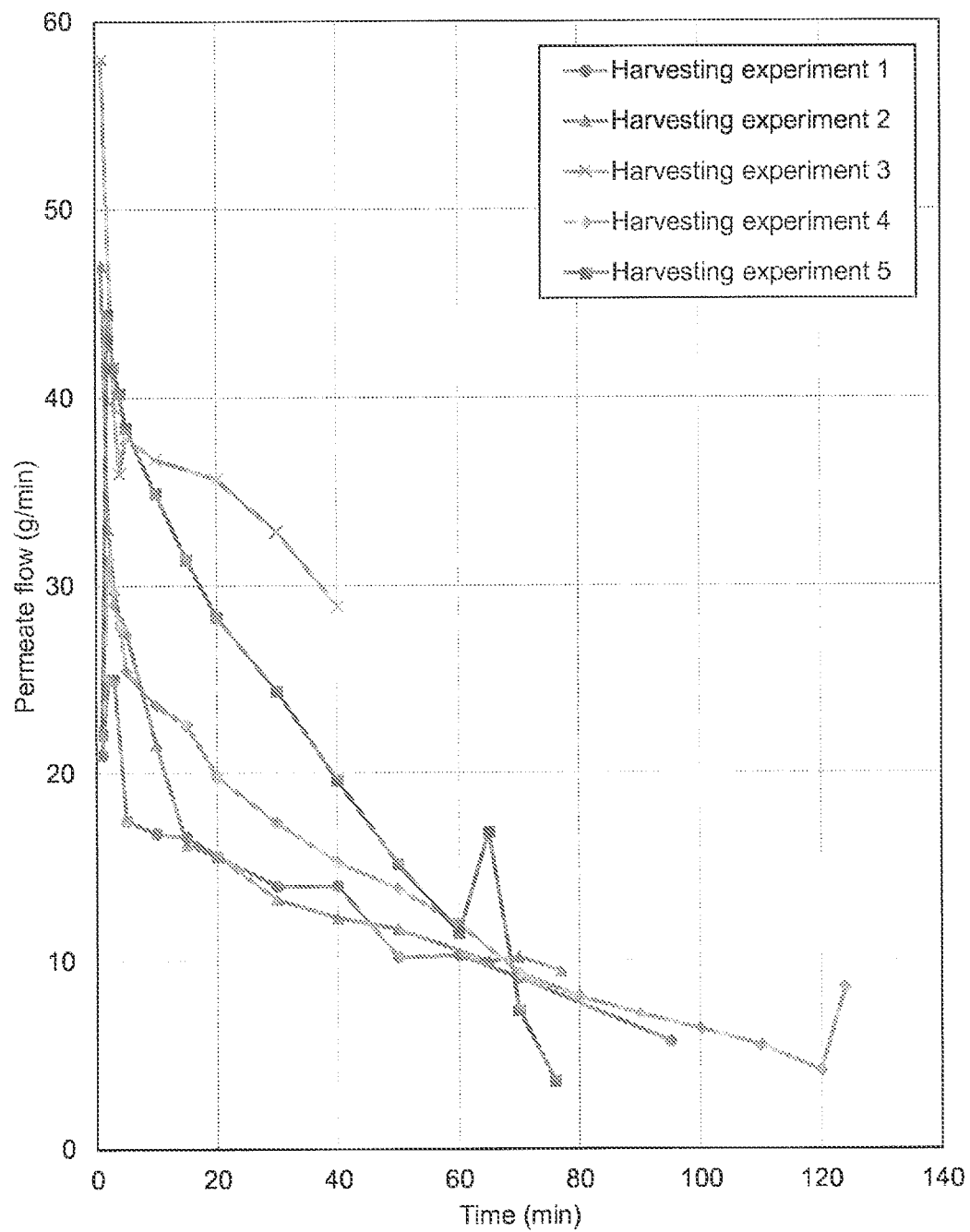
FIG. 3 is a diagram showing permeate flow during precipitated phytase harvesting by microfiltration.

Materials from examples 2 and 4 were used in five different precipitate harvesting tests. Harvesting was done by microfiltration using either two Sartorius Vivaflow 200 cassettes having 0.2 μm PES membranes or Pellicon 0.2 μm membranes. The aim was to keep the phytase-alginate complexes inside the membrane and remove as much as possible of the excess supernatant containing other proteins and high molecular weight compounds. Harvestings were made in room temperature. During harvesting proper stirring with magnetic stirrer was used for the retentate. During the harvesting permeate flow was monitored and harvesting was continued until around 4 times concentration factor was reached. Permeate formations and permeate flows are illustrated graphically in FIG. 2 and FIG. 3. In two of the harvesting test also washing step for harvested precipitate was done. Harvesting conditions and yields are represented in table 5. Precipitate yields were calculated based on soluble enzyme activities in permeates. These results show that microfiltration is feasible method to harvest and concentrate the phytase precipitate. These results also show that washing of the harvested precipitate is possible.

TABLE 5

Harvesting conditions and yields of *E. coli* phytase precipitates using microfiltration.

| Harvesting experiment | Precipitated material | Used cassette | Washing step | Concentration factor | Precipitate yield (%) |
|---|---|---|---|---|---|
| 1 | concentrate | Sartorius | no | 4.0 | 82 |
| 2 | concentrate | Sartorius | yes | 3.5 | 82 |
| 3 | concentrate | Sartorius | yes | 3.6 | 84 |
| 4 | filtrate | Pellicon | no | 3.9 | 70 |
| 5 | filtrate | Pellicon | no | 4.1 | 70 |

Example 7—Precipitate Harvesting by Vacuum Belt Filtration

Material for harvesting tests was prepared using the method in example 2. In this example instead of dry sodium alginate a stock solution of 0.4% (w/w) sodium alginate was used. Final precipitation conditions were: 0.19% (w/w) sodium alginate, 0.05 M sodium acetate buffer. Aimed FTU:mg of sodium alginate-ratio was 10 000 and calculated dry matter contents was 5.2% (w/w). Needed tap water and concentrate amounts were calculated so that aimed FTU:mg of sodium alginate-ratio and calculated dry matter contents was reached. Calculated precipitation yield of this batch was 75% analysed based on soluble activity in the filtrate.

Two precipitate harvesting experiments were performed. Harvesting was carried out with vacuum belt filtration test devise: BHS-nutsche (BHS-Filtration Inc.) Used filtration area was 56 cm$^2$ and used filter cloth was polypropylene (8 μm). Diatomite earth was used as filter aid. Filtrated materials and used washing liquids were cooled to around 10° C. prior to filtration.

In the first harvesting test 5 g of filter aid was mixed to 50 ml of precipitated phytase slurry. This suspension was filtrated with the test devise using −0.5 barg pressure. After 0'50 min's 40 ml of filtrate was achieved. After filtration the formed cake was dewatered. Calculated precipitated phytase yield of this harvesting test was 66% analysed based on precipitated activity in the dewatered filter cake.

In the second harvesting test 2.5 g of filter aid was mixed with to 50 ml of precipitated phytase slurry. This suspension was filtrated with the test devise using −0.5 barg pressure. After 3'30 min's 40 ml of filtrate was achieved. After the filtration formed cake was washed using 10 ml of tap water and dewatered. Formed cake was collected and re-slurred: 8.5 g of dewatered cake was mixed with 10 g of 3.1 (w/w) NaCl solution to dissolve the precipitated phytase. This solution was filtrated without additional filter aid with test devise using −0.5 barg pressure. Formed cake was dewatered. Calculated phytase yield of this harvesting test was 48% analysed based on soluble activity in the final filtrate.

These results show that harvesting of precipitated phytase with vacuum belt filtration was possible with diatomite earth as filter aid. Precipitate could also be dissolved and separated from the filter aid.

Example 8—Precipitate Harvesting by Centrifugation

Using the method in example 2, a batch precipitation was done. The precipitated material was a concentrate of *E. coli* phytase. Used precipitation conditions were the same as in batches 1 and 2 in the example 2. Calculated precipitation yield of this batch was 71% analysed based on soluble activity in supernatant. This precipitated *E. coli* phytase was used in the precipitate harvesting experiment.

Harvesting was carried out by centrifugation. For harvesting precipitated slurry was divided in two centrifugation bottles that were centrifuged 4000 rpm 10 minutes. After centrifugation excess supernatants were removed. This was repeated two times to collect all the precipitate. After centrifugation 4% (w/w) of dry $Na_2SO_4$ was added and mixed to the precipitated mass. Salt and precipitates were let to mix and dissolve in cold room overnight. After dissolving solutions were pooled and analysed. Calculated precipitation yield of the centrifugation was 72% analysed based on activity of the solubilized liquid. These results show that recovery of the phytase precipitate by centrifugation is feasible method.

Example 9—Precipitate Harvesting by Sedimentation

Figure 4:
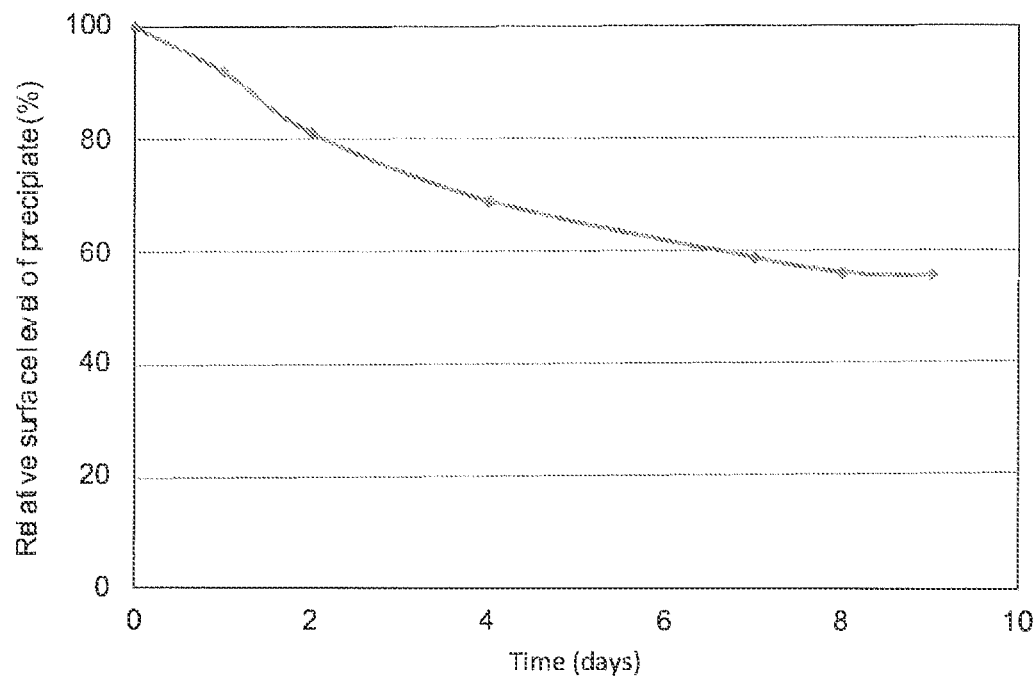
FIG. 4 is a diagram showing the relative height of precipitate surface level during settling experiment.

Same starting material as in example 8 was used also in this precipitate harvesting experiment. Sedimentation was used as harvesting method for the precipitate. 1 litre of precipitated phytase slurry was placed in storage bottle without mixing. The precipitate was let to settle on the bottle in cold room. Settling was observed by measuring the height of the surface level of the precipitate. Settling was continued for 9 days and after that excess supernatant was removed. Settling is illustrated graphically in FIG. 4. To dissolve the precipitate 4% (w/w) of dry $Na_2SO_4$ was added and mixed to the collected precipitate. Salt and precipitate was let to dissolve in cold room overnight. Calculated total precipitation yield of the sedimentation was 98%, but activity concentration level of the solubilized phytase-alginate solution was only 38% compared to the solution received in the example 8. These results show that recovery of the phytase precipitate by sedimentation is possible.

Example 10—Precipitate Harvesting by Dynamic Cross Flow Filtration

Material for these harvesting experiments was prepared using the same method as in example 7. For harvesting experiments Dynamic Crossflow Simulator DCF 152/s was used. The test material was re-suspended and filled into stirrer and cooled feeding vessel. The cooling was set to apply 5° C. operation temperature for all tests. Test matrix for harvesting tests are represented in table 6. With tested conditions it was not possible to harvest phytase precipitation from the slurry. Gained permeates from tests 1-3 were turbid and had almost the same appearance as the feed slurry. During these tests most likely an electrochemical reaction, caused by zeta potential of the ceramic material, destroyed the phytase-polyanion complex upon contact. This allowed the single molecules to pass the pores of ceramic disc in soluble form and rebuild the solid complex afterward. In addition to ceramic disc a stainless steel disc having 1.3 μm cutoff was tested, but it did not improve permeate clarity. Tests with lower shear stress (300 rpm) were also performed during the trials, but no improvement in permeate turbidity was achieved. These results show reversible charge based complex formation of phytase and polyanion and the importance of material and technique selection for solid-liquid separation.

TABLE 6

Test matrix of precipitate harvesting experiment with dynamic cross flow filtration.

| Test | Disc porosity (nm) | Base material | Process conditions | Rotational speed (rpm) |
|---|---|---|---|---|
| 1 | 200 | $Al_2O_3$ | 4-5° C. | 930 |
| 2 | 30 | $TiO_2$ | TMP (trans membrane | |
| 3 | 7 | $MgAl_2O_4$ | pressure) | |
| 4 | 1300 | 312L stainless steel | 0.3-1.2 bar | |

Example 11—Supernatant Recycling

Supernatants collected from examples 8 and 9 precipitations were used in this test. Precipitated material was a concentrate of *E. coli* phytase. The aim of this tests was to study if supernatant from phytase-polyanion precipitation can be used as diluent in next phytase precipitation. Total of eight precipitation tests using two different supernatants were made. Also, one reference precipitation without supernatant using the method in example 2 batches 1 and 2 was made. Instead of dry sodium alginate 1% stock solution of sodium alginate was used to make the reagent solutions. The same concentrate amount as in the reference precipitation was used in all supernatant recycling tests. Final test conditions and results are represented in Table 7. Precipitation was observed during concentrate addition only if also sodium alginate was added to the test. This indicates that there is no sodium alginate left anymore in the supernatants after phytase-polyanion precipitate separation because sodium alginate is needed to be added again to induce phytase precipitation. Activity analysis were made from precipitated samples. These results show that supernatant from phytase precipitation can be recycled and used again in the next batch precipitation to make the reagent solution. In the recycling tests 1, 2, 7 and 8 no precipitations were seen due to lack of polyanion in the recycled supernatant.

TABLE 7

Experiment conditions of supernatant recycling in precipitation tests.

| Recycling test | Reagent solution composition | Supernatant from | Sodium alginate (%, w/w) | Sodium acetate (M) | Soluble FTU activity (%) of total activity |
|---|---|---|---|---|---|
| 1 | supernatant | example 9 | nd | nd | no precipitation |
| 2 | supernatant | example 8 | nd | nd | no precipitation |
| 3 | supernatant and sodium alginate | example 9 | 0.18 | nd | 42 |
| 4 | supernatant and sodium alginate | example 8 | 0.18 | nd | 41 |
| 5 | supernatant, sodium alginate and buffer | example 9 | 0.18 | 0.05 | 53 |
| 6 | supernatant, sodium alginate and buffer | example 8 | 0.18 | 0.05 | 51 |
| 7 | supernatant and buffer | example 9 | nd | 0.05 | no precipitation |
| 8 | supernatant and buffer | example 8 | nd | 0.05 | no precipitation |
| 9 | tap water, sodium alginate and buffer (reference) | | 0.18 | nd | 33 |

Example 12—Preparation of Liquid Product

Material from example 8 harvested by centrifugation was used as a starting material for preparing the stabilized liquid formulations 1 and 2 of phytase-alginate complex. For formulation 3 precipitated material was taken from batch 4 of example 2. Precipitate was harvested by sedimentation.

To prepare formulations dry powders of sodium sulphate, sorbitol, citric acid and tri-sodium citrate, and 35% (w/w) sodium benzoate solution were added to the harvested and solubilized precipitates. Two of the liquid products were formulated with sorbitol and one without sorbitol. Solutions were mixed with magnetic stirrer thoroughly before cold storage. Final formulation conditions are presented in table 8. Activities of these formulations were the same or higher compared to the commercial liquid phytase product without polyelectrolyte precipitation treatment used as a reference. Enzyme activity of formulation 1 was 1.5× higher compared to the reference and activity concentration of formulation 2 was 1.1× higher than the reference. Activity concentration of formulation 3 was at the same level as in the reference. These results show that by using precipitated phytase it is possible to increase enzyme concentration in liquid products.

TABLE 8

Formulation conditions of liquid products prepared of precipitated *E. coli* phytase.

| Formulation | Solubilized precipitate (%) | Sodium sulphate (%, w/w) | Sorbitol (%, w/w) | Citric acid (%, w/w) | Tri-sodium citrate (%, w/w) | Sodium benzoate (%, w/w) | Sodium alginate (%, w/w) | pH |
|---|---|---|---|---|---|---|---|---|
| 1 | 91.2 | 3.9 | 0.0 | 0.5 | 2.7 | 0.3 | 1.0 | 4.7 |
| 2 | 72.0 | 4.0 | 19.7 | 0.5 | 2.2 | 0.4 | 0.8 | 4.7 |
| 3 | 72.4 | 3.9 | 19.7 | 0.5 | 2.3 | 0.3 | 0.9 | 4.3 |

Example 13—Preparation of Dry Product

Retentates from microfiltration harvesting experiments in example 6 were used as starting material in spray drying tests to produce dry product of phytase-alginate solid complex. Büchi Mini Spray Dryer B-290 was used for sample drying. Six different spray dryings were performed. Drying additive, either PEG 4000 or trehalose, was used in three of these experiments. Additive was added right before spray drying. PEG was added as 50% (w/w) liquid to the harvested precipitate solution while stirring properly. Trehalose was added as dry powder to the precipitate solution while stirring properly. Precipitate solution amounts with or without additives fed to the spray dryer varied from 570 g to 760 g. During spray drying precipitated solution were kept in room temperature under proper stirring. During spray drying inlet temperature was kept near 130° C. and pump value near 30% so that outlet temperature would stay near 75° C. Activity and dry matter contents were analysed from precipitate solutions and final spray dried powders to calculate drying yields. All dryings were successful and no difficulties occurred during dryings. Final spray drying conditions and yields are represented in Table 9. These results show that precipitated material can be formulated to dry products by spray drying with or without drying additives.

TABLE 9

Spray drying conditions and yields of precipitated *E. coli* phytase.

| Drying sample | Material from | Drying additive | Powder dry matter (%, w/w) | Material loss to chamber (%) | Drying yield (%) |
|---|---|---|---|---|---|
| 1 | Harvesting 1 | | 95.7 | 37 | 86 |
| 2 | Harvesting 2 | | 95.9 | 38 | 86 |
| 3 | Harvesting 3 | 1% (w/w) PEG 4000 | 94.9 | 31 | 100 |
| 4 | Harvesting 3 | 2% (w/w) PEG 4000 | 95.8 | 27 | 100 |
| 5 | Harvesting 4 | | 94.6 | 64 | 90 |
| 6 | Harvesting 5 | 1% (w/w) trehalose | 95.1 | 56 | 91 |

Example 14—Storage Stability of Liquid Product (Soluble Complex)

Formulations from example 12 were taken under accelerated storage stability study. Storage time was 8 weeks. For stability study each of the formulated liquids was divided in 15 ml falcon tubes closed with caps, 5 ml of liquid per tube. One tube was prepared for each storage time point. All sample tubes were placed into 37° C. climate chamber. From each time point one sample tube was taken to freezer before activity analysis. Phytase activities from each storage time point were compared to the starting point phytase activity.

Figure 5:
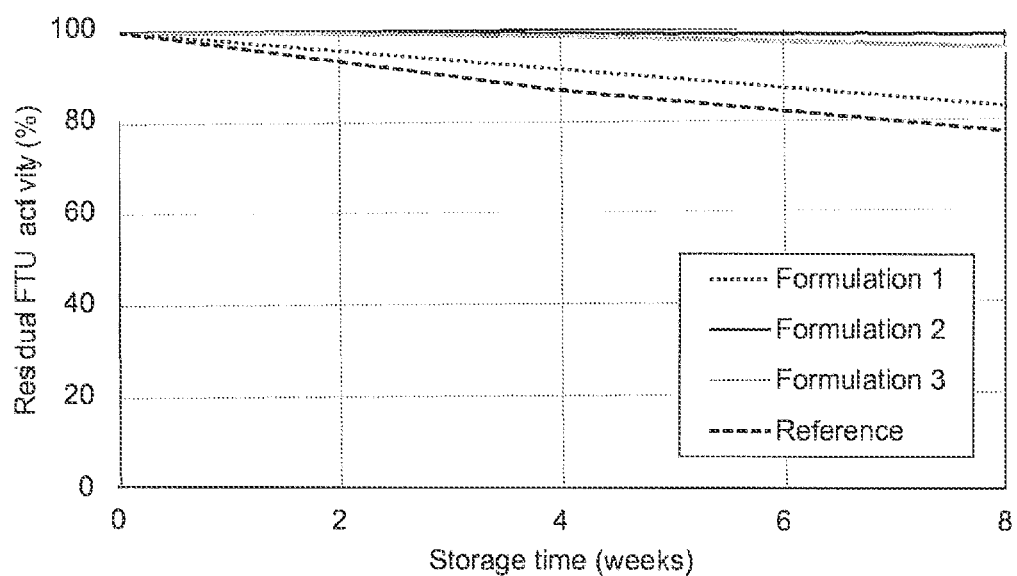
FIG. 5 is a diagram showing the residual phytase activities of E. coli phytase liquid formulations during storage at temperature 37° C.

Commercial liquid phytase product without polyelectrolyte precipitation treatment stored in the same manner was used as a reference. Activity concentration levels of the studied formulations varied. Activity concentration of formulation 1 was 1.5× higher compared to the reference and activity concentration of formulation 2 was 1.1× higher than the reference. Enzyme activity of formulation 3 was at the same level as reference. Stability results are illustrated graphically in FIG. 5. The results show improved stability when phytase-polyanion complex has been formulated to liquid product compared to the reference product without complex formation.

Example 15—Storage Stability of Dry Product (Solid Complex)

Using the method in example 2 a series of 2 L batch precipitations were prepared. The precipitated material was a concentrate of *E. coli* phytase. Used precipitation conditions were following: 0.05 M sodium acetate buffer, 0.46% (w/w) sodium alginate, 4000 FTU:mg of sodium alginate-ratio, calculated dry matter 5.2%. After precipitation these batches were combined and excess of liquid part was removed to receive precipitate slurry having dry matter 12.3%. This slurry was spray dried using the method in example 13 in exception that no drying additive was used. During spray drying inlet temperature was kept near 132° C. and pump value near 34% so that outlet temperature would stay near 75° C. Activity and dry matter contents were analysed from precipitate solution and final spray dried powder to calculate drying yields. Powder dry matter was 96.1% and drying yield was 100%.

Figure 6:
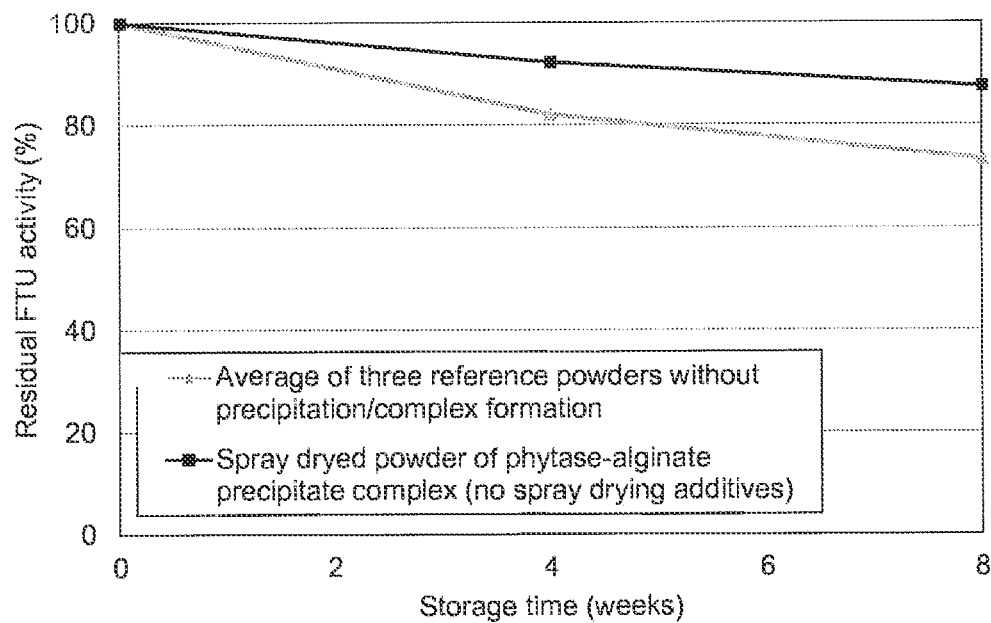
FIG. 6 is a diagram showing the residual phytase activities of E. coli phytase powder formulations during storage at temperature 40° C.

This dry product was taken under accelerated storage stability study. Storage time was 8 weeks. For stability study the dry powder was divided in 50 ml falcon tubes closed with caps, 8-10 g in each tube. For each storage time points one tube was prepared. All sample tubes were placed to 40° C. climate chamber. From each time point one sample tube was taken to freezer before activity analysis. Phytase activities from each storage time points were compared to the starting point phytase activity. Stability results are illustrated graphically in FIG. 6. These results show improved stability when phytase-polyanion complex has been formulated to dry product: curve showing residual activity at different time points was 19% higher level after storage of 8 weeks at 40° C. compared to the reference commercial dry phytase products without precipitation/complex formation studied in the same manner.

Example 16—Pelleting Test

Dry powder samples 1, 2, 3 and 4 from spray drying experiments in example 13 were used to study heat stability by a standardized pelleting tests at an independent institute (Danish Technological Institute, Kolding, Denmark). Test articles were mixed into mash feeds, that were treated in a conditioner with hot water steam resulting in different mash feed temperatures before pelleting. Recoveries were calculated from enzyme activities analysed in the pellets after heat treatment compared to the enzyme activity in the mash feed without conditioning and pelleting. These recoveries were compared to commercial dry phytase product without precipitation/complex formation tested in the same manner. Recovery improvement percentages are represented graphically in FIG. 7. These results show that heat stability in pellets after treatment at higher conditioning temperatures can be increased by using polyelectrolyte precipitated and spray dried phytase.

Example 17—Precipitation Using Different Sodium Alginate Types

The effect of different sodium alginates to precipitate *E. coli* phytase was studied. A series of batch precipitation experiments were performed using five different sodium alginate products: one from Fluka (71238), one from Sigma (W201502) and three from FMC (Manucol D H, Manucol D H MCLDHP and Manucol LD). For batch precipitations reagent solutions were prepared by adding 1 M sodium acetate buffer (nominal pH 3.6) and dry sodium alginate in tap water. Dry powders were let to dissolve and reagent solutions were stored in cold room overnight. Phytase concentrate was added to the reagent solutions at room temperature while stirring properly with magnetic stirrer and let precipitate at cold 1 hour. Needed tap water and concentrate amounts were calculated so that aimed 10 000 FTU:mg of polyanionic compound-ratio and calculated dry matter contents of 5.2% was reached. Final precipitation conditions were: 0.17% (w/w) sodium alginate and 0.05 M sodium acetate. After precipitation soluble enzyme activities were determined to calculate precipitation yield. The results are represented in table 10. These results show that different sodium alginate types have different effect on the precipitation yield.

TABLE 10

Effect of different sodium alginate types on the soluble phytase activity and precipitation yield.

| Used sodium alginate | pH | Ratio (FTU:mg of sodium alginate) | Soluble enzyme activity of total activity (%) | Precipitation yield (%) |
|---|---|---|---|---|
| Fluka (71238) | 4.15 | 10 680 | 21 | 79 |
| Sigma (W201502) | 4.17 | 10 859 | 27 | 73 |
| Manucol DH (FMC) | 4.29 | 10 794 | 6 | 94 |
| Manucol DH MCLDHP (FMC) | 4.15 | 10 973 | 26 | 74 |
| Manucol LD (FMC) | 4.26 | 10 842 | 6 | 94 |

Example 18—Screening of Right Ratio of Phytase and Polyanionic Compound

The effect of FTU:mg polyanionic compound ratio with different polyanionic compounds was studied. A series of 2 g batch precipitation experiments were performed using concentrate of *E. coli* phytase. Studied polyanionic compounds were sodium alginate, sodium hyaluronate and sodium polypectate. Studied ratios varied from 1200 to 9800. For batch precipitations reagent solutions were prepared in 2 ml Eppendorf tubes by adding 1 M sodium acetate buffer (nominal pH 3.6) and stock solution of selected polyanionic compounds to tap water. Used polyanionic stock solutions were: 2% (w/w) sodium alginate, 2% (w/w) sodium polypectate, 0.5% (w/w) sodium hyaluronate. Phytase concentrate was added to the reagent solutions at room temperature and vortexed properly, whereupon phytase-polyanionic complex was rapidly formed. Needed tap water and concentrate amounts were calculated so that aimed FTU:mg of polyanionic compound-ratio and calculated dry matter contents was reached. Final sodium acetate concentration in all experiments was 0.05 M. Final precipitation conditions and activity yields are represented in table 11 and soluble activity curves are illustrated graphically in FIG. 8. Precipitation yields were calculated based on soluble phytase activity in supernatants. These results show that phytase can be precipitated with all studied polyanions and precipitate yield can be improved by changing ratio of FTU:mg polyanionic compound.

TABLE 11

Effect of different FTU:mg of polyanionic compound -ratios and different polyanionic compound on the *E. coli* phytase precipitation yield.

| Screening experiment | Polyanion (%, w/w) | Ratio (FTU:mg of polyanion) | Polyanionic compound | Calculated dry matter (%, w/w) | Precipitation yield (%) |
|---|---|---|---|---|---|
| 1 | 0.90 | 1900 | sodium alginate | 5.9 | 96 |
| 2 | 0.60 | 2800 | sodium alginate | 5.6 | 100 |
| 3 | 0.45 | 3800 | sodium alginate | 5.5 | 100 |
| 4 | 0.36 | 4600 | sodium alginate | 5.3 | 100 |
| 5 | 0.30 | 5700 | sodium alginate | 5.3 | 98 |
| 6 | 0.26 | 6400 | sodium alginate | 5.3 | 94 |
| 7 | 0.23 | 7200 | sodium alginate | 5.2 | 89 |
| 8 | 0.18 | 9400 | sodium alginate | 5.2 | 74 |
| 9 | 1.44 | 4800 | sodium polypectate | 5.6 | 72 |
| 10 | 1.20 | 5700 | sodium polypectate | 5.4 | 60 |
| 11 | 1.03 | 6500 | sodium polypectate | 5.3 | 57 |
| 12 | 1.45 | 5400 | sodium hyaluronate | 5.3 | 88 |
| 13 | 1.22 | 6300 | sodium hyaluronate | 5.2 | 79 |
| 14 | 1.02 | 7700 | sodium hyaluronate | 5.3 | 71 |
| 15 | 0.90 | 8600 | sodium hyaluronate | 5.2 | 66 |
| 16 | 0.80 | 9800 | sodium hyaluronate | 5.2 | 57 |

Example 19—Precipitation Using Phytic Acid as Polyanionic Compound Alone and in Combination with Sodium Alginate Phytic acid—substrate of phytase—was studied as polyanionic compound to see its phytase precipitating potential. Also precipitation using combination of sodium alginate and phytic acid was studied. A series of 2 g batch precipitation experiments were performed using concentrate of *E. coli* phytase. For batch precipitations reagent solutions were prepared in 2 ml Eppendorf tubes by adding 1 M sodium acetate buffer (nominal pH 3.6) and stock solution of selected polyanionic compounds to tap water. Used polyanionic stock solutions were: 2% (w/w) sodium alginate and 5% (w/w) phytic acid. Phytase concentrate was added to the reagent solutions cooled down in ice bath and stirred properly, whereupon phytase-polyanionic complex was rapidly formed. Needed tap water and concentrate amounts were calculated so that aimed FTU:mg of polyanionic compound-ratio and calculated dry matter contents was reached. Final sodium acetate concentration in all experiments was 0.05 M. Final precipitation conditions and yields are represented in table 12. Precipitation yields were calculated based on soluble protein concentration in supernatants compared to the total protein concentration. These results show that phytase can be precipitated with combination of the studied polyanions. They also show transient precipitation of phytase if phytic acid is used alone as precipitating polyanion at the studied conditions.

TABLE 12

Precipitation conditions and yields of six *E. coli* phytase precipitation batches.

| Screening experiment | Sodium alginate (%, w/w) | Phytic acid (%, w/w) | Total of polyanions (%, w/w) | Ratio (FTU:mg of total polyanions) | pH | Calculated dry matter (%, w/w) | Precipitation yield (%) |
|---|---|---|---|---|---|---|---|
| 17 |  | 1.46 | 1.46 | 1200 | 1.74 | 5.2 | transient precipitation |
| 18 | 1.26 | 0.20 | 1.46 | 1200 | 3.90 | 5.3 | 60.8 |
| 19 | 1.46 |  | 1.46 | 1200 | 4.35 | 5.3 | 49.0 |
| 20 |  | 0.88 | 0.88 | 2000 | 2.02 | 5.2 | transient precipitation |
| 21 | 0.78 | 0.10 | 0.88 | 2000 | 4.05 | 5.2 | 64.5 |
| 22 | 0.89 |  | 0.89 | 2000 | 4.32 | 5.2 | 62.9 |

Example 20—Effect of Concentrate Dilution Factor on Precipitated Phytase Yield

The effect of dilution of phytase concentrate on phytase precipitation was studied. A series of 2 g batch precipitation experiments were performed using concentrate of *E. coli* phytase. Precipitations were done using sodium alginate as polyanionic compound and aimed FTU:mg of sodium alginate-ratio was 4000. For batch precipitations reagent solutions were prepared in 2 ml Eppendorf tubes by adding 1 M sodium acetate buffer (nominal pH 3.6) and 2% (w/w) sodium alginate stock solution to tap water. Phytase concentrate was added to the reagent solutions at room temperature and vortexed properly, whereupon phytase-polyanion complex was rapidly formed. Needed tap water and concentrate amounts were calculated so that aimed FTU:mg of polyanionic compound-ratio and calculated dry matter contents was reached. Final precipitation conditions and activity yields are represented in table 13. Precipitation yields were calculated based on soluble phytase activity in supernatants. These results show that precipitation yield can be increased even further by increasing dilution of phytase concentrate, which means lower dry matter content in the precipitation.

TABLE 13

Effect of *E. coli* phytase concentrates dilution on soluble phytase activity in polyelectrolyte precipitation.

| Experiment | Calculated total dry matter (%) | Sodium alginate (%, w/w) | Sodium acetate (M) | Soluble enzyme activity of total activity (%) | Precipitation yield (%) |
|---|---|---|---|---|---|
| 11 | 11.5 | 0.96 | 0.05 | 3.0 | 97.0 |
| 12 | 9.9 | 0.80 | 0.05 | 1.5 | 98.5 |
| 13 | 8.2 | 0.68 | 0.05 | 0.9 | 99.1 |
| 14 | 7.0 | 0.58 | 0.05 | 0.5 | 99.5 |
| 15 | 6.2 | 0.52 | 0.05 | 0.3 | 99.7 |
| 16 | 5.5 | 0.45 | 0.05 | 0.2 | 99.8 |

Example 21—Effect of Concentrate Dilution Factor on Activity Level and Purity of Formulated Liquid End Product The effect of phytase concentrate dilution to certain dry matter level on activity and purity of formulated liquid end products was studied. First a series of 40 g batch precipitations were prepared using concentrate of *E. coli* phytase. Sodium alginate was used as polyanionic compound and aimed FTU:mg of sodium alginate-ratio was 4000. For batch precipitations reagent solutions were prepared by adding 1 M sodium acetate buffer (nominal pH 3.6) and 2% (w/w) sodium alginate stock solution to tap water. Phytase concentrate was added to the reagent solutions at room temperature and stirred properly with magnetic stirrer, whereupon phytase-polyanionic complex was rapidly formed. Needed tap water and concentrate amounts were calculated so that aimed FTU:mg of sodium alginate-ratio and calculated dry matter contents was reached. Final precipitation conditions are represented in table 14.

TABLE 14

Experiment conditions of *E. coli* phytase batch precipitations.

| Experiment | Sodium alginate (%, w/w) | Sodium acetate (M) | Calculated dry matter (%, w/w) |
|---|---|---|---|
| 17 | 0.82 | 0.05 | 9.7 |
| 18 | 0.69 | 0.05 | 8.1 |
| 19 | 0.58 | 0.05 | 7.0 |
| 20 | 0.51 | 0.05 | 6.2 |

Next precipitates were harvested by centrifugation. After centrifugation as much as possible of supernatant was removed. After that phytase-alginate precipitates were dissolved by adding dry sodium sulphate and dry sorbitol so that final formulation conditions of 4% (w/w) sodium sulphate and 20% (w/w) of sorbitol were reached. Precipitates were let to dissolve in cold room overnight under agitation. Experiments with lowest dry matter content, which also means the highest dilutions, were easier to dissolve. Phytase activities and protein concentrations were analysed from final formulated liquids. For relative activity level activities (as FTU/g) of formulations 2, 3 and 4 were compared to the activity of formulation 1. For product purification factor calculated FTU/mg of protein values were compared to the FTU/mg of protein value of commercial liquid phytase product without polyelectrolyte precipitation treatment. Final formulation conditions and product purification are represented in table 15. These results show that more concentrated products are possible to achieve with higher purity by optimizing dilution of phytase concentrate.

TABLE 15

Formulation conditions of dissolved E. coli phytase precipitates.

| Formulation | Precipitation dry matter (%, w/w) | Sodium sulphate (%, w/w) | Sorbitol (%, w/w) | Relative activity level (%) | Product purification factor |
|---|---|---|---|---|---|
| 4 | 9.7 | 4.0 | 20.1 | 100 | 2.8 |
| 5 | 8.1 | 4.0 | 20.4 | 82 | 2.4 |
| 6 | 7.0 | 4.0 | 20.0 | 76 | 2.2 |
| 7 | 6.2 | 4.0 | 20.1 | 57 | 2.1 |

Example 22—Precipitation of Different Bacterial Phytase

Potential of sodium alginate to precipitate another bacterial phytase was studied. *Buttiauxella* phytase was used as starting enzyme material. In order to prepare phytase liquid suitable for precipitation 1 g of dried granule was suspended in 10 g of 25 mM sodium acetate buffer solution at pH 4. Liquid was separated and purified by gel filtration using the same sodium acetate buffer. After that batch precipitation was started by adding 2% (w/w) sodium alginate solution little by little to 5 g of purified enzyme material. Amount of added sodium alginate was measured and appearance of the solution was observed during sodium alginate addition. The results are represented in table 16.

TABLE 16

Physical appearance of *Buttiauxella* phytase precipitation during sodium alginate addition.

| Phytase in 25 mM sodium acetate pH 4 after gel filtration (%, w/w) | Sodium alginate (%, w/w) | Aimed FTU:mg of sodium alginate -ratio | Visual appearance |
|---|---|---|---|
| 99.8 | 0.004 | 8 000 | hazy |
| 99.8 | 0.005 | 7 000 | slightly turbid |
| 99.8 | 0.005 | 6 000 | slightly turbid |
| 99.7 | 0.006 | 5 000 | turbid |
| 99.6 | 0.007 | 4 000 | completely turbid |
| 99.5 | 0.010 | 3 000 | completely turbid |
| 99.3 | 0.015 | 2 000 | completely turbid + visible precipitate particles |

Adding of sodium alginate was stopped when visible precipitate particles were observed. Samples for activity analysis were taken from this final precipitated solution. Precipitation conditions and precipitated enzyme activity yield are represented in table 17. Precipitation yield was calculated based on soluble phytase activity in supernatant compared to total activity. These results show that sodium alginate can be used successfully to precipitate another bacterial phytase then used in most of the experiments.

TABLE 17

Experiment conditions and precipitation yield of *Buttiauxella* phytase batch precipitation.

| Phytase in 25 mM sodium acetate pH 4 after gel filtration (%, w/w) | Sodium alginate (%, w/w) | Aimed FTU:mg of sodium alginate - ratio | Precipitation yield (%) |
|---|---|---|---|
| 99.3 | 0.015 | 2000 | 85 |

Example 23—Precipitation of Fungal Phytase

Potential of sodium alginate to precipitate fungal phytase was studied. Four batch precipitations were done using concentrates of *Aspergillus* phytase as starting enzyme material. Precipitations were made in 15 ml tubes and total volumes of the precipitations were 10 ml. Reagent solutions were prepared by mixing 1 M sodium acetate buffer (nominal pH 3.6), 2% (w/w) sodium alginate stock solution and tap water in tubes. Phytase concentrate was added to the reagent solutions at room temperature and vortexed properly to enable complex formation. Needed tap water and concentrate amounts were calculated so that aimed FTU:mg of sodium alginate-ratio and calculated dry matter contents were reached. Final precipitation conditions and precipitated enzyme activity yields are represented in table 18. Precipitation yields were calculated based on soluble phytase activity in supernatants. These results show that sodium alginate precipitation can be used successfully to precipitate also fungal phytases.

TABLE 18

Experiment conditions and precipitation yields of *Aspergillus* phytase batch precipitations.

| Fungal phytase precipitation experiment | Sodium alginate (%, w/w) | Sodium acetate (M) | Aimed FTU:mg of sodium alginate - ratio | Calculated dry matter (%, w/w) | Precipitation yield (%) |
|---|---|---|---|---|---|
| 1 | 0.36 | 0.05 | 2000 | 3.6 | 26.2 |
| 2 | 0.18 | 0.05 | 4000 | 3.5 | 18.4 |
| 3 | 0.21 | 0.05 | 2000 | 2.0 | 55.1 |
| 4 | 0.10 | 0.05 | 4000 | 2.0 | 12.2 |

Example 24—Phytase-Alginate Complex Dissolving with Calcium Chloride

*E. Coli* phytase precipitation was done in similar manner as described in the Example 4. Precipitate was harvested by sedimentation. In this example dissolving of the harvested precipitate was done using $CaCl_2$ instead of $Na_2SO_4$ that has been used in the previous precipitate dissolving examples. To dissolve the harvested precipitate dry calcium chloride dihydrate was added and mixed to the harvested precipitate with and without other additives to achieve final experiment conditions shown in the table 19 below.

TABLE 19

Experiment conditions of dissolved *E. coli* phytase precipitates.

| Experiment | Harvested phytase-alginate precipitate % (w/w) | $CaCl_2$ x2H$_2$O % (w/w) | Tri-sodium citrate dihydrate % (w/w) | Sorbitol % (w/w) | Na-benzoate % (w/w) | pH | Observation |
|---|---|---|---|---|---|---|---|
| 21 | 98.2 | 0.7 |     |     | 0.37 | 5.3 | dissolved, some gel |
| 22 | 96.3 | 0.7 | 2.0 |     | 0.35 | 4.7 | dissolved, viscous |
| 23 | 91.5 | 0.4 | 2.1 | 5.0 | 0.37 | 4.8 | dissolved, viscous |
| 24 | 92.4 | 0.4 | 1.0 | 5.1 | 0.37 | 4.6 | dissolved, some gel, viscous |

These results show that phytase-alginate precipitate dissolves even more effectively by adding calcium chloride compared to sodium sulphate or sodium chloride used as dissolving salt. High viscosity and gel noticed in the experiment liquids indicate $Ca^{2+}$ induced gelation of alginate at these phytase-alginate complex dissolving conditions. Existence of $Ca^{2+}$ is therefore considered beneficial in liquid formulation in the case there is a need to prevent re-precipitation of phytase as complex with alginate. At the same time these results show that $CaCl_2$) can not be used as a precipitant of phytase bound alginate like used with other enzymes in prior art. On the contrary, $CaCl_2$) works as dissolving agent in the case of phytase. These results indicate that existence of $Ca^{2+}$ in the phytase precipitation phase would lead to ineffective precipitation or would prevent precipitation of phytase completely.

Different non-binding example aspects and embodiments of the present invention have been illustrated in the foregoing. The embodiments are used merely to explain selected aspects or steps that may be utilized when implementing the present invention. Some embodiments may be presented herein only with a reference to a certain aspect of the invention. It should be appreciated that the embodiments may apply to other aspects of the present invention, as well. Consequently, any appropriate combination of the embodiments and the aspects may be formed. Any combination of aspects or embodiments as disclosed herein may also be made without at least one non-essential feature disclosed in an aspect or embodiment.

What is claimed is:

1. A method of preparing a phytase composition comprising
   i) providing an aqueous medium comprising phytase;
   ii) preparing a reversible phytase-polyanion complex in an enzymatically active form by adding a polyanion selected from an alginic acid, a pectic acid, a hyaluronic acid, a salt thereof, or any combination thereof, to the aqueous medium; and
   iii) directly recovering the reversible phytase-polyanion complex in an enzymatically active form to obtain the phytase composition;
   wherein no $Ca^{2+}$ is added to the aqueous medium during the method.

2. The method of claim 1, wherein the phytase composition is dehydrated to obtain a dry product.

3. The method of claim 1, further comprising dissolving of the phytase composition to obtain a liquid product.

4. The method of claim 3, further comprising dehydrating the phytase composition to obtain a dry product.

5. The method of claim 4, further comprising dissolving the dry product to obtain a reconstituted product.

6. The method of claim 1, further comprising washing the phytase composition.

7. The method of claim 6, wherein the phytase composition is dehydrated to obtain a dry product.

8. The method of claim 6, further comprising dissolving of the phytase composition to obtain a liquid product.

9. The method of claim 8, further comprising dehydrating the phytase composition to obtain a dry product.

10. The method of claim 9, further comprising dissolving the dry product to obtain a reconstituted product.

* * * * *